United States Patent
Yoshioka et al.

(10) Patent No.: US 10,185,804 B2
(45) Date of Patent: Jan. 22, 2019

(54) INPUT APPARATUS AND INFORMATION PROCESSING SYSTEM

(71) Applicant: Sony Corporation, Tokyo (JP)

(72) Inventors: Shigeatsu Yoshioka, Kanagawa (JP); Hidaka Uchida, Tokyo (JP); Yoichi Mizutani, Saitama (JP); Seiji Miyama, Kanagawa (JP); Toru Mitome, Tokyo (JP)

(73) Assignee: Sony Corporation, Tokyo (JP)

(*) Notice: Subject to any disclaimer, the term of this patent is extended or adjusted under 35 U.S.C. 154(b) by 150 days.

(21) Appl. No.: 13/901,750

(22) Filed: May 24, 2013

(65) Prior Publication Data

US 2014/0013280 A1    Jan. 9, 2014

(30) Foreign Application Priority Data

Jul. 3, 2012    (JP) .................. 2012-149725

(51) Int. Cl.
| | | |
|---|---|---|
| *G06F 17/21* | (2006.01) | |
| *G06F 17/30* | (2006.01) | |
| *G06F 3/0484* | (2013.01) | |
| *G06F 19/00* | (2018.01) | |

(52) U.S. Cl.
CPC ........ *G06F 19/321* (2013.01); *G06F 3/04842* (2013.01); *G06F 3/04845* (2013.01); *G06F 17/30244* (2013.01); *G06F 17/212* (2013.01); *G06F 17/3056* (2013.01);
(Continued)

(58) Field of Classification Search
CPC ............... G06F 3/0482; G06F 3/04842; G06F 3/04845; G06F 3/0486; G06F 19/321; G06F 3/0488; G06F 2203/04806; G06F 3/04886; G06F 3/048; G06F 2203/04803; G06F 17/30244; G06F 17/30047; G06F 3/03547; G06F 1/1626; G06F 2203/04808; G06F 3/041; H04N 1/00442; H04N 2201/325; H04N 5/44591; H04N 21/4312; H04N 2201/3273; H04N 1/0044; H04N 1/00411; G06Q 10/10; G06Q 50/24; G06Q 50/22; G06T 19/00; G06T 3/40; G06T 1/00; G06T 2207/30004; G06T 5/009; G06T 2219/2016; G06T 3/60; Y10S 707/99933; Y10S 707/913; G09G 2340/145; G09G 2340/04; G09G 2340/045
USPC ........ 715/838, 835, 764, 716, 763; 345/173, 345/619, 156, 660, 428, 634, 649, 661;
(Continued)

(56) References Cited

U.S. PATENT DOCUMENTS

| 5,596,698 A | * | 1/1997 | Morgan | .................. 715/863 |
| 6,424,332 B1 | * | 7/2002 | Powell | .................. 345/156 |

(Continued)

FOREIGN PATENT DOCUMENTS

JP    2006-519443 A    8/2006

*Primary Examiner* — Kevin L Young
*Assistant Examiner* — Maria S Ayad
(74) *Attorney, Agent, or Firm* — Michael Best & Friedrich LLP (57) ABSTRACT

Provided is an input apparatus, including: a touch panel configured to receive input operation of at least selecting a medical image, the medical image being displayed on a display area of a display apparatus; and an operation input unit configured to receive spatial operation of the medical image as continuous input, the medical image being displayed on the display area.

19 Claims, 7 Drawing Sheets

(52) U.S. Cl.
 CPC ............... *G06F 2203/04803* (2013.01); *G06T 2200/24* (2013.01); *G06T 2207/30004* (2013.01)

(58) Field of Classification Search
 USPC ........... 382/305, 128, 298; 348/E5.104, 564, 348/588; 707/999.003
 See application file for complete search history.

(56) References Cited

U.S. PATENT DOCUMENTS

| | | | | |
|---|---|---|---|---|
| 8,624,837 | B1* | 1/2014 | Han | G06F 1/1615 345/157 |
| 2004/0267122 | A1* | 12/2004 | Nadadur et al. | 600/440 |
| 2005/0197536 | A1* | 9/2005 | Banik | A61B 1/00059 600/179 |
| 2006/0274928 | A1* | 12/2006 | Collins et al. | 382/132 |
| 2006/0288004 | A1* | 12/2006 | Toriyama | 707/6 |
| 2007/0226646 | A1* | 9/2007 | Nagiyama | G06F 3/016 715/784 |
| 2008/0018615 | A1* | 1/2008 | Zadesky | G06F 1/1626 345/173 |
| 2008/0150911 | A1* | 6/2008 | Harrison | 345/173 |
| 2009/0054755 | A1* | 2/2009 | Shiibashi | G06F 19/321 600/407 |
| 2010/0034442 | A1* | 2/2010 | Minakuchi et al. | 382/128 |
| 2011/0242055 | A1* | 10/2011 | Kim | G06F 3/042 345/175 |
| 2012/0001868 | A1* | 1/2012 | Na | G06F 3/041 345/174 |
| 2012/0064946 | A1* | 3/2012 | Voetberg et al. | 455/566 |
| 2012/0170727 | A1* | 7/2012 | Karnalkar et al. | 379/93.09 |
| 2012/0183191 | A1* | 7/2012 | Nakamura | 382/128 |
| 2012/0238363 | A1* | 9/2012 | Watanabe | H04N 21/472 463/31 |

\* cited by examiner

INPUT APPARATUS AND INFORMATION PROCESSING SYSTEM

BACKGROUND

This technology relates to an input apparatus configured to operate a viewer, which is used to observe a medical image.

According to a browsing method in the past, a client viewer reads an image (tile image), which is divided into tiles and stored in an image server, based on a navigation operation instruction from a user. The client viewer displays the read image. A user merely selects a portion, which he wishes to browse. As a result, a system is capable of recognizing and displaying the corresponding tile image.

Further, for example, Japanese Patent Application Laid-open No. 2006-519443 discloses the following technology. First, a client viewer requests for image data at a certain resolution. The image data is in a virtual slide image file. Next, a server system obtains a compressed block of image data, which includes image data of which resolution is close to the requested resolution. The server system sends the data block to the client. Next, the client zooms in/out the image data, and presents the image at the requested resolution.

SUMMARY

According to Japanese Patent Application Laid-open No. 2006-519443 and in general, in a case of observing a medical image by using a viewer, a general-purpose computer is mostly used as a viewer computer. In this case, a keyboard or a mouse is used as an input apparatus when observing a medical image. User-friendliness when observing a medical image is poor.

After a keyboard and a mouse, a touch panel is used when observing a medical image, but it still has problems. First, let's say that a user inputs information in a touch panel based on an absolute position. In this case, it is necessary to prepare a touch panel, of which resolution is the same as the resolution of a high-resolution window that is used to observe a medical image. This is not realistic. Further, let's say that a user inputs information in a touch panel based on a relative position. In this case, for example, it is necessary to repeat a small movement little by little in order to input an instruction to move a pointer for a long distance. It takes a lot of trouble with input.

In view of the above-mentioned circumstances, it is desirable to provide an input apparatus and an information processing system, each of which is capable of improving user-friendliness of a viewer that is used to observe a medical image.

(1) According to an embodiment of this technology, there is provided an input apparatus, including: a touch panel configured to receive input operation of at least selecting a medical image, the medical image being displayed on a display area of a display apparatus; and an operation input unit configured to receive spatial operation of the medical image as continuous input, the medical image being displayed on the display area.

According to this technology, operation to the input apparatus is mainly divided into two kinds of input operation, i.e., operation of selecting a medical image and spatial operation of a displayed medical image. A device suitable for the operation of selecting a medical image is used, and the device receives input operation. Another device suitable for the spatial operation is used, and the device receives input operation. As a result, user-friendliness of the input apparatus may be improved.

Here, one operation of selecting a medical image is to select a target medical image from a list by using a GUI. The list is a group of candidates to be displayed on the display area of the display apparatus. Another operation of selecting a medical image is to drag and drop a selected medical image in a display area, on which the selected medical image is to be displayed, and to display the selected medical image. As described above, operation using a touch panel is suitable for the operation of selecting a medical image.

Further, spatial operation of a medical image is, for example, operation of zooming in/out, moving, and rotating the display area of a medical image, which is displayed on the display area of the display apparatus. Further, an example of continuous input operation is operation of keeping on pressing a button. Another example of continuous input operation is operation of keeping on tilting an analog stick in one direction. In a case of zooming in the display area of the medical image continuously, the button is continuously pressed. In a case of moving the display area in one direction continuously, the analog stick is continuously tilted in one direction. As described above, the spatial operation is continuous operation. As described above, a button or an analog stick is suitable for spatial operation.

(2) According to an embodiment of this technology, there is provided the input apparatus, in which the operation input unit is configured to receive an instruction to change a display area of the medical image as the spatial operation of the medical image, the medical image being displayed on the display area, the instruction being at least one of instructions to zoom in/out, move, and rotate the medical image.

According to this technology, the spatial operation of the medical image is operation to change the display area of the medical image displayed on the display area. Specifically, the spatial operation of the medical image is at least one of zooming in/out operation, moving operation, and rotating operation. As described above, such operation is suitable to input information by using a button or an analog stick. It is possible to improve user-friendliness of zooming in/out operation, moving operation, and rotating operation by using such devices.

(3) According to an embodiment of this technology, there is provided the input apparatus further including: a display unit spatially corresponding to the touch panel; and a controller configured to display a set on the display unit, the set being a group of at least one medical image, to display a low-resolution window on the display unit, the low-resolution window being a low-resolution image of a display area on the display apparatus, to send an instruction to the display apparatus to call up a medical image on the display area of the display apparatus, the medical image being selected from the displayed set by a user via the touch panel, and to display an image on the low-resolution window, the image being a low-resolution image of the medical image.

According to this technology, the resolution of the display of the touch panel is low. Because of this, it is not possible to display the display area of the display apparatus, of which definition is high in order to observe a medical image, on the display of the touch panel as it is. Because of this, it is not possible to input an absolute position of the display of the display apparatus, in the touch panel as it is. In view of this, a low-resolution image of the display area on the display apparatus is obtained. The entire screen of the display apparatus is displayed on the touch panel. As a result, it is possible to input an absolute position of the display of the display apparatus, on the touch panel. Because of this, it is possible to avoid the trouble of having to input operation little by little repeatedly in a case of relative position input.

(4) According to an embodiment of this technology, there is provided the input apparatus, in which the controller is configured to display, on the display unit, a thumbnailed medical image in the set, to detect that a user flicks and taps the thumbnail displayed on the touch panel to thereby select the thumbnailed medical image, and to display a medical image on the display unit, the medical image corresponding to the thumbnailed medical image.

According to this technology, the thumbnailed medical images are displayed on the display of the touch panel. A user flicks and taps one of the thumbnails, to thereby select an image. As a result, it is possible to further improve user-friendliness of the input apparatus.

(5) According to an embodiment of this technology, there is provided the input apparatus further including: a case accommodating the touch panel, the operation input unit, and the display unit, in which the touch panel is arranged on one main surface side of the case, and the input apparatus further comprises a touch pad, the touch pad being configured to receive at least selection of the medical image, the touch pad being arranged on a second main surface of the case, the second main surface being opposite to a first main surface, the touch panel being arranged on the first main surface.

According to this technology, a touch panel and in addition a touch pad are used to receive input operation of selecting a medical image. Because of this, the number of received operation is smaller than the number of operation input received only by a touch panel. Because of this, it is not necessary to make input operation complicated in order to distinguish one operation from another. Each operation may be made simple. It is possible to further improve user-friendliness of operation input.

(6) According to an embodiment of this technology, there is provided the input apparatus in which the controller is configured to recognize handwritten data, the data input in at least one of the touch panel and the touch pad, and to reflect the recognized data in display on the display apparatus.

According to this technology, certain handwritten data is input in the touch panel or the touch pad. Then, the controller recognizes the data. The data is reflected in display on the display apparatus. Because of this, a user is capable of inputting an instruction with an effort smaller than the effort in a case of firstly selecting an instruction from a menu. As a result, it is possible to further improve user-friendliness of the input apparatus.

(7) According to an embodiment of this technology, there is provided the input apparatus in which the controller is configured to recognize the data as a numerical value, and to divide the display area into a number, the number corresponding to the recognized numerical value.

According to this technology, a user traces a number shape on the touch panel or the touch pad. Then, the controller recognizes the handwritten data as a numerical value. Then, the controller divides the display area. Because of this, a user is capable of inputting an instruction to divide a display area with an effort smaller than the effort in a case of firstly selecting an instruction to divide a display from a menu and inputting the number of division. Because of this, it is possible to further improve user-friendliness of the input apparatus.

(8) According to an embodiment of this technology, there is provided an information processing system, including: a display apparatus including a display area, a medical image being displayed on the display area; and an input apparatus including a touch panel configured to receive input operation of at least selecting a medical image, the medical image being displayed on the display area, and an operation input unit configured to receive spatial operation of the medical image as continuous input, the medical image being displayed on the display area.

As described above, according to this technology, it is possible to improve user-friendliness of a viewer, which is used to observe a medical image.

These and other objects, features and advantages of the present disclosure will become more apparent in light of the following detailed description of best mode embodiments thereof, as illustrated in the accompanying drawings.

DETAILED DESCRIPTION OF EMBODIMENTS

Hereinafter, an embodiment of the present disclosure will be described with reference to the drawings.

[Outline of this Technology]

This technology relates to an input apparatus. The input apparatus is connected to a viewer computer via a wireless LAN or the like and is used. A viewer runs in the viewer computer. The viewer is software, and is used to observe medical images. The input apparatus roughly divides input operation into two kinds of input operation, i.e., discrete input operation and continuous input operation. The input apparatus uses an input device suitable for the discrete input operation and another input device suitable for the continuous input operation. With this configuration, information may be input easily. An observer of a medical image may easily select a medical image to be observed by using the input apparatus, and may easily operate the input apparatus when he observes the selected medical image in detail.

Note that the above-mentioned "discrete input operation" is, for example, the following operation using a touch panel. That is, an observer touches an object displayed on a touch panel, and drags the object to a predetermined position. Further, the "continuous input operation" is, for example, the following operation using a button or an analog stick. That is, an observer keeps on pressing a button, and keeps on tilting an analog stick in one direction.

Figure 1:
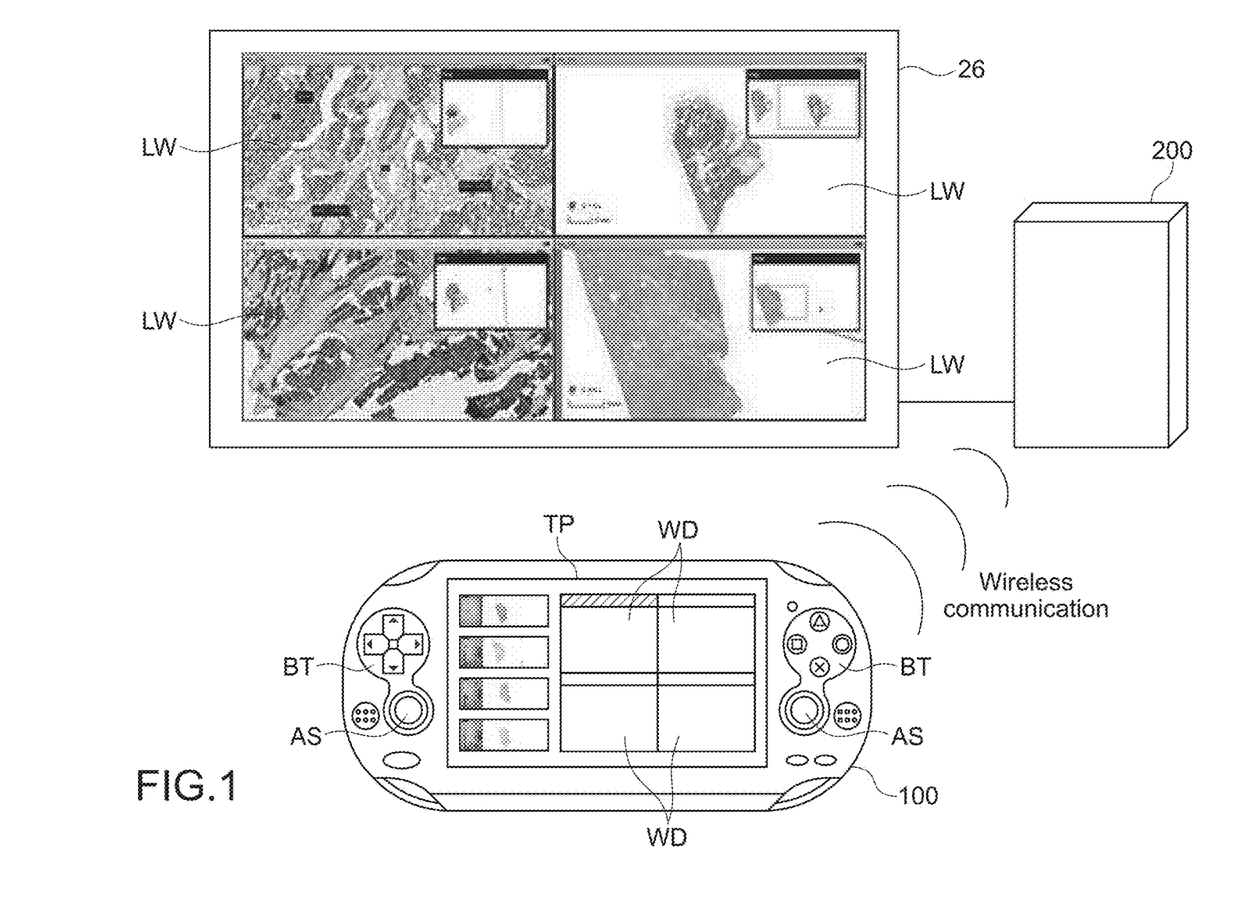
FIG. 1 is a diagram schematically showing an environment in which this technology is used.

FIG. 1 is a diagram schematically showing an environment in which this technology is used. A user, who observes a medical image, has an input apparatus 100 of this technology on hand. Further, the input apparatus 100 communicates with a viewer computer 200 via wireless communication. The viewer computer 200 includes a display unit 26. Medical images are displayed on the display unit 26. The input apparatus 100 includes a touch panel TP at the center of the front surface. The input apparatus 100 further includes buttons BT and analog sticks AS on both sides of the touch panel TP.

In FIG. 1, medical images are displayed on four divided windows LW (display areas) on the display unit 26. Symbols of four divided windows WD are displayed on the right portion of the touch panel TP of the input apparatus 100. The four divided windows WD correspond to the four divided windows LW, respectively. The windows LW on the display unit 26 correspond to the windows WD on the touch panel TP one to one. For example, the upper right window LW corresponds to the upper right window WD. Note that a list of thumbnails of the medical images is displayed on the left portion of the touch panel TP.

A user operates the input apparatus 100, which he has with his hand, and selects a medical image to be observed from the list of the medical images on the left portion of the touch panel TP. Then, the user drags and drops the selected medical image on one of the symbols of the four windows WD on the right portion of the touch panel TP. Information on the selected medical image and information on the window LW, on which the selected medical image is to be displayed, are transmitted to the viewer computer 200 via wireless communication. The viewer computer 200 displays the selected medical image on the selected window LW in response to the transmitted information.

When a user observes a medical image displayed on the window LW, he inputs operation of zooming in/out, moving, and rotating an image, for example. The user inputs such operation by using the buttons BT and the analog sticks AS of the input apparatus 100.

Note that the four divided windows LW and the four divided windows WD are described above. This is merely an example. Alternatively, an undivided window LW and an undivided window WD may be used. Alternatively, two, three, or five or more divided windows LW, and two, three, or five or more divided windows WD may be used.

Further, in the above-mentioned example, the list of the thumbnails of the medical images is displayed on the left portion of the touch panel, and the symbol windows WD are displayed on the right portion. However, the display position is not limited to this example. For example, the list of the thumbnails of the medical images may be displayed on the right portion and the symbol windows WD may be displayed on the left portion. Because of this, a left-handed user may easily drag and drop a medical image.

Figure 2:
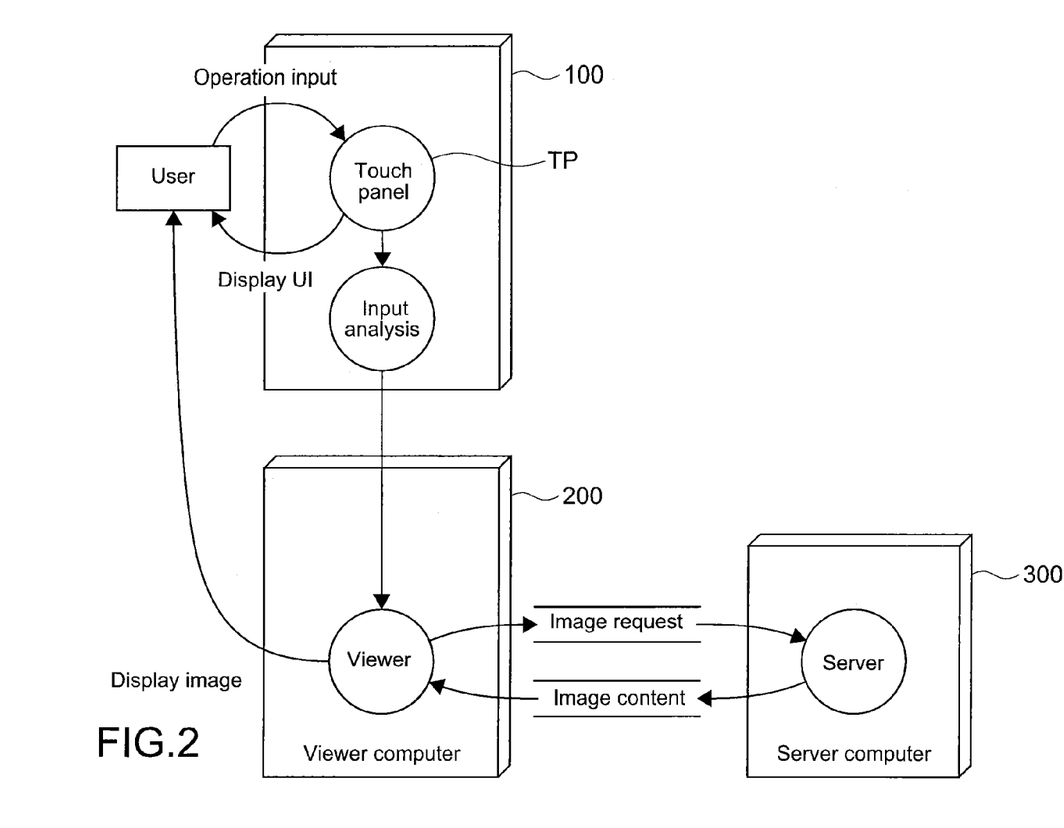
FIG. 2 is a diagram briefly showing the flow of information using a touch panel of an input apparatus 100 of this technology.

FIG. 2 is a diagram briefly showing the flow of information using the touch panel of the input apparatus 100 of this technology. Note that FIG. 2 is based on the premise that a server computer 300 stores medical images.

First, the input apparatus 100 displays the list of the thumbnails of the medical images and the symbol windows WD on the touch panel TP as UIs (User Interfaces). A user selects a target medical image and a window LW, on which the medical image is to be displayed, by using the UIs. The input apparatus 100 analyzes the input based on the selection. The input apparatus 100 transmits information on the selected medical image and on the selected window LW to the viewer of the viewer computer 200.

The viewer sends an image request to the server computer 300 based on the information on the selected medical image.

A server program of the server computer 300 retrieves a medical image in response to the received image request. The server program of the server computer 300 replies image content to a viewer of the viewer computer 200. The viewer displays a medical image, which is the received image content, on the window LW selected by the user.

The flow from operation of the touch panel to display of a medical image on the window LW of the viewer has been described above.

[Problems of Related Technology and Solutions]

Here, problems of a related technology and solutions of this technology will be briefly described again.

(1) In the past, if a user observes a medical image by using a viewer of a viewer computer, the user uses one of a touch panel, a button, and an analog stick to input operation. Operation input by using a touch panel is suitable to select a medical image and to operate a window of the viewer. However, operation input by using a touch panel is not suitable to zoom in/out, move, and rotate (hereinafter, referred to as viewing operation) a medical image displayed on a window for a long time. To the contrary, a button and an analog stick are suitable for such viewing operation. However, a button and an analog stick are not really suitable to select a medical image and to operate a window.

As described above, a tradeoff relation is established between a touch panel, and a button and an analog stick. In view of this, this technology provides both the touch panel, and the button and analog stick. Operation suitable for each device is allocated to the device. As a result, operation input may be optimized.

(2) Further, in the past, if touch operation is input in an absolute position of a touch panel, it is necessary to use a touch panel, of which resolution is the same as the display resolution of a display. However, in general, the extremely high-definition display unit 26 is used to observe a medical image. It is not realistic to use a touch panel, of which resolution is the same as the resolution of the extremely high-definition display unit 26.

In view of this, touch input in an absolute position is not adopted. It is necessary to operate a pointer in a relative position by using a touch panel, of which resolution is lower than the display resolution of a display. In this case, for example, if an area, in which a user is capable of moving a mouse, is narrow, it is necessary to move the mouse little by little repeatedly in order to move a pointer by a necessary amount. As is this example, it is necessary to wipe a touch panel little by little repeatedly to thereby move a pointer, which is troublesome and problematic.

In view of this, according to this technology, symbols of viewer windows, which are displayed on the high-definition display unit 26, are displayed on the low-resolution touch panel. As a result, a user is capable of inputting operation in an absolute position of the low-resolution touch panel.

Low-resolution symbols of the viewer windows are displayed on the touch panel. As a result, it is possible to input operation in an absolute position of the low-resolution touch panel. Because of this, since it is possible to input operation in an absolute position, it is possible to avoid the trouble of having to input operation little by little repeatedly in a case of input such as relative input using an operation surface having a limited area.

Note that examples of a method of creating a symbol include the following methods. A window displayed on the high-definition display unit 26 may be downconverted to thereby obtain a low-resolution symbol. Alternatively, a window displayed on the high-definition display unit 26 may be replaced by a low-resolution icon, which symbolizes the window LW displayed on a high-definition window.

(3) The following is not a problem of a related technology. A touch pad may be provided in addition to a touch panel in order to improve user-friendliness in a case where a user inputs operation by using a touch panel. For example, the touch panel TP is provided on the front surface of the input apparatus 100, and a touch pad is provided on the back surface of the input apparatus 100.

With this structure, the touch panel TP on the front surface and the touch pad on the back surface share operation input in a touch panel. The number of the kinds of operation input in each of the touch panel TP and the touch pad is made small. Operation input in each of the touch panel TP and the touch pad is made simple. As a result, user-friendliness may be improved.

Note that the touch panel TP and the touch pad may share operation input in a touch panel as follows. The touch panel on the front surface may be used for operation, which may raise no problem even if a finger that touches an operation target partially hides the operation target displayed on the touch panel. Further, the touch pad on the back surface may be used for operation, which may raise a problem if a finger that touches an operation target hides the operation target displayed on the touch panel.

[Configuration of Viewer Computer 200]

Next, the hardware configuration of the viewer computer 200 will be described. A dedicated apparatus or a general-purpose computer may be used as a viewer computer as long as the viewer computer is capable of executing a viewer. Here, the hardware configuration in a case where a general-purpose computer is used will be described.

Figure 3:
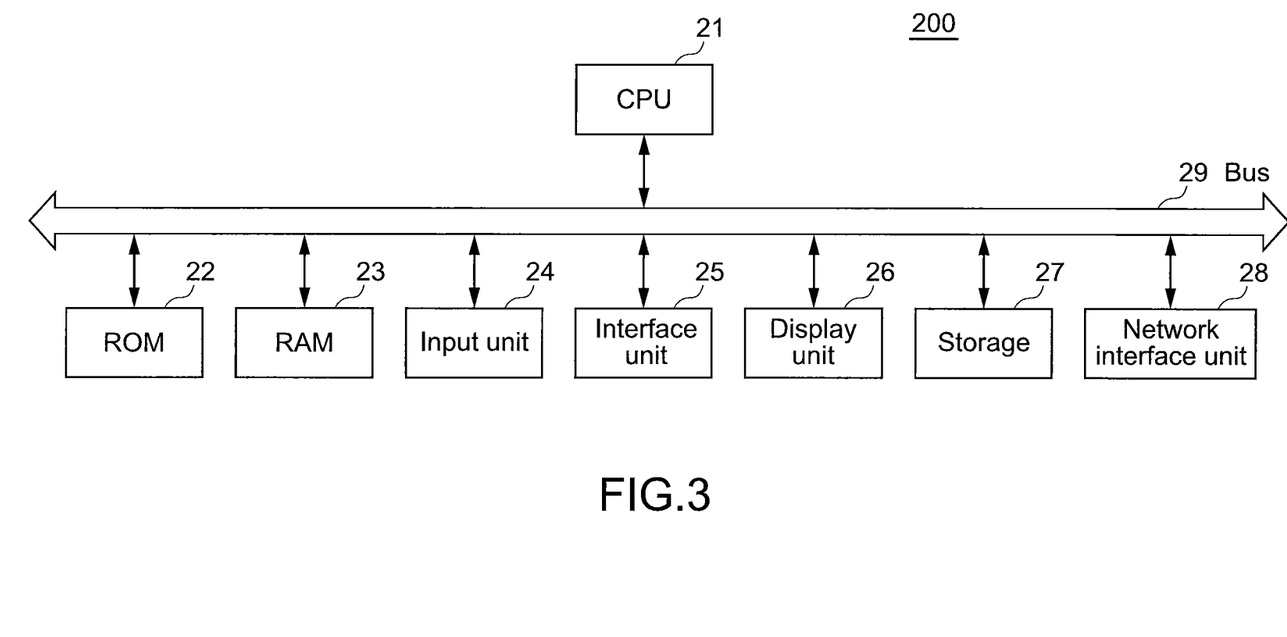
FIG. 3 is a block diagram showing the hardware configuration of a viewer computer 200 of this technology.

FIG. 3 is a block diagram showing the hardware configuration of the viewer computer 200 of this technology.

The viewer computer 200 includes a CPU (Central Processing Unit) 21, a ROM (Read Only Memory) 22, a RAM (Random Access Memory) 23, and an input unit 24. The CPU 21 executes arithmetic control. The RAM 23 is a work memory for the CPU 21. Instructions are input in the input unit 24 depending on operation by a user. The viewer computer 200 further includes an interface unit 25, the display unit 26, storage 27, a network interface unit 28, and a bus 29 connecting them each other.

Programs for executing various processes are stored in the ROM 22. The network interface unit 28 may be connected to the input apparatus of this technology via a wired LAN, a wireless LAN, Bluetooth (registered trademark), or the like.

A liquid crystal display, an EL (Electro Luminescence) display, a plasma display, or the like may be used as the display unit 26 for displaying an image. Note that a high-definition display, of which resolution is enough high to observe a medical image, is used for a liquid crystal display or the like. A magnetic disk such as a HDD (Hard Disk Drive), a semiconductor memory, an optical disk, or the like may be used as the storage 27.

The CPU 21 expands a program, which corresponds to an instruction supplied from the input unit 24 out of a plurality of programs stored in the ROM 22, in the RAM 23. The CPU 21 appropriately controls the display unit 26 and the storage 27 based on the expanded program.

[Configuration of Input Apparatus 100 (No. 1)]

Figure 4:
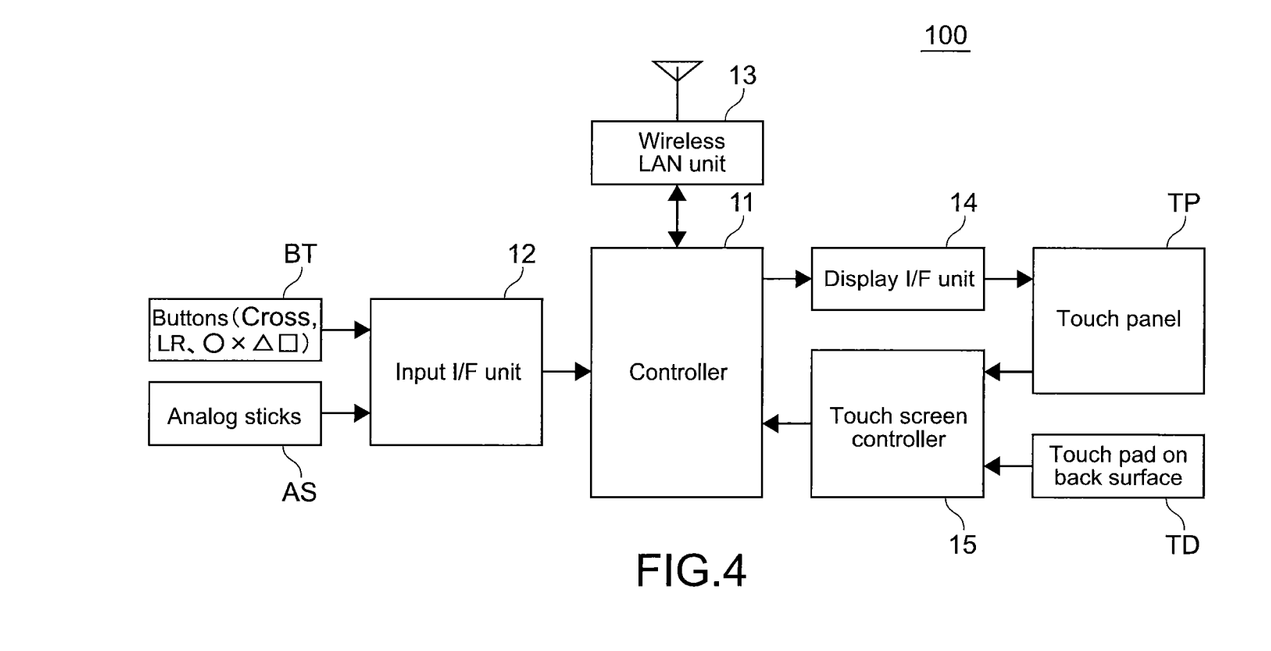
FIG. 4 is a block diagram showing the hardware configuration of the input apparatus 100 of this technology.

Next, the hardware configuration of the input apparatus 100 will be described. FIG. 4 is a block diagram showing the hardware configuration of the input apparatus 100 of this technology.

The input apparatus 100 includes a controller 11, an input I/F unit 12, a wireless LAN unit 13, a display I/F unit 14, a touch screen controller 15, the touch panel TP, and a touch pad TD on the back surface.

The controller 11 controls the entire input apparatus 100. Input in the buttons BT and the analog sticks AS is transmitted to the controller 11 via the input I/F unit 12. The controller 11 analyzes the transmitted information. The controller 11 sends an analysis result to the viewer computer 200 via the wireless LAN unit 13.

Further, the controller 11 receives information on a high-resolution window from the viewer computer 200 via the wireless LAN unit 13. The high-resolution window is displayed on the display unit 26 of the viewer computer 200. The controller 11 creates a low-resolution window based on the information on the high-resolution window. The low-resolution window is obtained by making the high-resolution window to have low resolution. The controller 11 displays the low-resolution window on the touch panel TP via the display I/F unit 14.

Similarly, the controller 11 receives thumbnails of medical images from the viewer computer 200 via the wireless LAN unit 13. The controller 11 creates a tray, i.e., a set of medical images of each patient. The controller 11 displays the tray on the touch panel TP.

Further, the controller 11 receives operation input in the touch panel TP and the touch pad TD on the back surface via the touch screen controller 15. The controller 11 analyzes the received input. Further, the controller 11 updates an image displayed on the touch panel TP based on the analysis result. The controller 11 sends the analysis result to the viewer computer 200 via the wireless LAN unit 13.

The input I/F unit 12 receives input in the buttons BT and the analog sticks AS. The input I/F unit 12 transmits the input to the controller 11.

The wireless LAN unit 13 wirelessly communicates with the network interface unit 28 of the viewer computer 200. As a result, communication between the controller 11 and the viewer computer 200 is established. Any wireless standard may be employed as long as wireless communication is established.

The display I/F unit 14 controls display on the windows on the touch panel TP. The display I/F unit 14 displays the list of the thumbnails of the medical images and the low-resolution windows WD or the symbol windows WD, which are transmitted from the controller 11, on the touch panel.

The touch screen controller 15 receives touch input in the touch screen of the touch panel TP on the front surface of the input apparatus 100 and in the touch pad TD on the back surface of the input apparatus 100. The touch screen controller 15 supplies the touch input to the controller 11.

[Configuration of Input Apparatus 100 (No. 2)]

Figure 5:
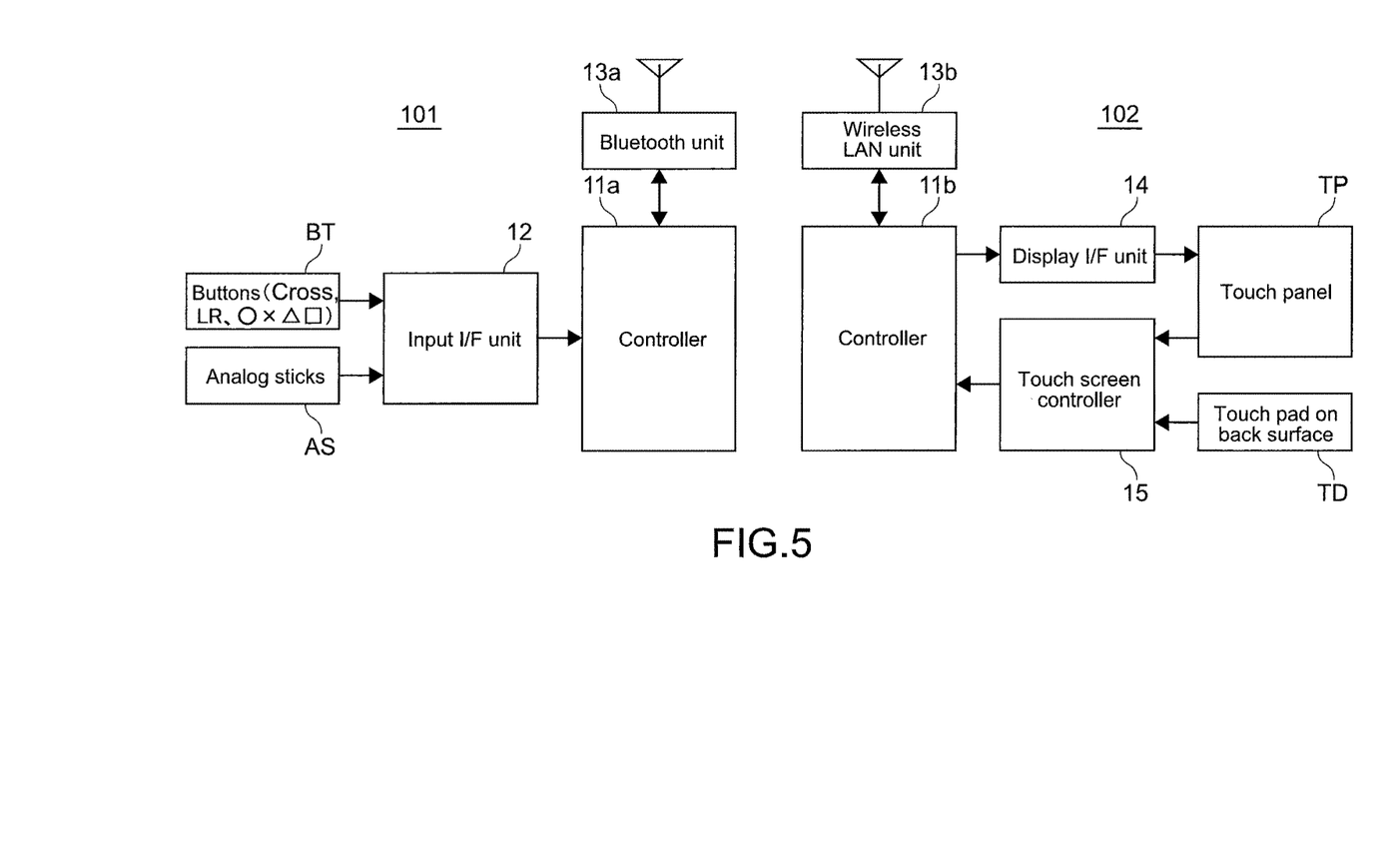
FIG. 5 is a diagram showing the hardware configuration of an input apparatus 101 and the hardware configuration of an input apparatus 102.

Next, the hardware configuration of an input apparatus 101 and the hardware configuration of an input apparatus 102 will be described. In the above description, the input apparatus 100 includes both the buttons BT and the analog sticks AS, and the touch panel TP and the touch pad TD. To the contrary, here, separate input apparatuses will be described. The separate input apparatuses include the input apparatus 101 only including the buttons BT and the analog sticks AS, and the input apparatus 102 only including the touch panel TP and the touch pad TD.

FIG. 5 is a diagram showing the hardware configuration of the input apparatus 101 and the hardware configuration of the input apparatus 102.

The hardware configuration of the input apparatus 101 and the hardware configuration of the input apparatus 102 have the following characteristics. Since the input apparatuses are separate, there are two separated main bodies. The one controller 11 of the input apparatus 100 is divided into two controllers 11a and 11b.

Further, the one wireless LAN unit 13 of the input apparatus 100 is divided into a Bluetooth (registered trademark) unit 13a of the input apparatus 101, and a wireless LAN unit 13b of the input apparatus 102. Note that, here, for example, the Bluetooth (registered trademark) unit is provided based on the premise that the input apparatus 101 wirelessly communicates with the viewer computer 200 via Bluetooth (registered trademark). Alternatively, any wireless standard may be employed as long as wireless communication is executed.

Note that the function of each block of FIG. 5 is the same as the function of each block of the all-in-one input apparatus 100. Alternatively, the function of each block of FIG. 5 is obtained by dividing each function of the all-in-one input apparatus 100. Overlapped description will be omitted.

[Operation Input Shared by Touch Panel and Touch Pad]

Figure 6:
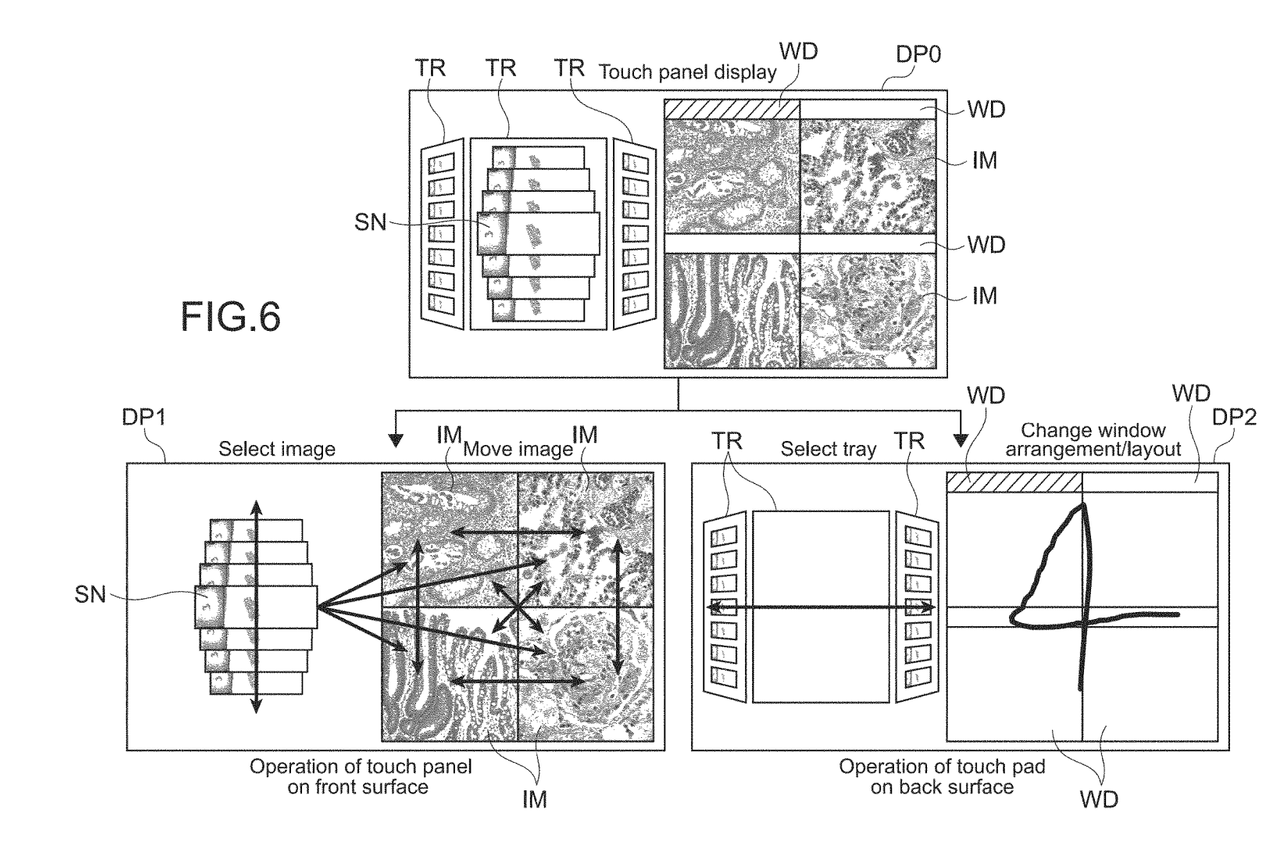
FIG. 6 is a diagram showing an example in a case where a touch panel TP and a touch pad TD share operation input.

The touch panel TP and the touch pad TD on the back surface of the input apparatus 100 share operation input. Next, an example of this situation will be described. FIG. 6 is a diagram showing an example in a case where the touch panel TP and the touch pad TD share operation input. The sharing of operation input described below is actually an example. Operation input, which is assigned to the touch panel TP in this example, may be assigned to the touch pad TD. Operation input, which is assigned to the touch pad TD in this example, may be assigned to the touch panel TP. Alternatively, a different sharing method may be employed.

First, a display DP0 on the upper part of FIG. 6 is actually displayed on the touch panel TP. Thumbnails SN of medical images are arrayed in a list. The lists are sorted for each tray TR. The lists for each tray TR are displayed on the left portion of the display DP0. Further, the four windows WD are displayed on the right portion. An image IM, which is a part of a medical image, is displayed on the window WD.

The display DP0 is divided into objects controlled by using the touch panel TP, and objects controlled by using the touch pad TD. Displays DP1 and DP2 on the lower part of FIG. 6 show this situation. Note that the displays DP1 and DP2 are prepared for explaining this situation. That is, the displays DP1 and DP2 are not displayed on the touch panel actually.

A user operates the thumbnails SN of medical images displayed on the left portion of the display DP1, and the images IM displayed on the right portion, by using the touch panel TP. Further, a user operates the trays TR, each of which stores a set of the thumbnails SN, displayed on the left portion of the display DP2, and the windows WD displayed on the right portion, by using the touch pad TD.

A user directly flicks and taps one of a plurality of thumbnails displayed on the left portion of the display DP1 with his finger or the like, to thereby select a medical image to be observed. Further, a user directly drags and drops the thumbnail of the selected image on one of the positions of the four images IM on the right portion of the display DP1. As a result, the user selects the position, on which the image IM is displayed. Further, a user directly drags the image IM displayed on the right portion of the display DP1. As a result, the user changes the position, on which the image IM is displayed.

Further, a user wipes the left area of the touch pad TD, which is on the back surface of the input apparatus 100, in the lateral direction. As a result, the user selects the tray TR, which includes a set of medical images to be observed and displayed on the left portion of the display DP2.

Further, a user traces a number shape on the right area of the touch pad TD. As a result, the user instructs to divide the window WD into the windows WD, the number of which corresponds to the traced number. The right portion of the display DP2 shows the following situation. A user traces (hereinafter, referred to as gestures) the "4" shape. As a result, the user instructs to divide each of the windows WD, LW into "4" windows. The controller 11 analyzes the operation input, and recognizes "4". The controller 11 divides the window WD into four windows WD. As described above, the controller 11 recognizes a handwritten letter input in the touch panel TP and the touch pad TD. The controller 11 behaves depending on the recognized letter.

As described above, the touch panel TP and the touch pad TD share input operation. As a result, the number of the kinds of operation input in each device is decreased. Operation is made simple. As a result, overall user-friendliness may be improved.

[Operation Example of Input Apparatus 100]

Figure 7:
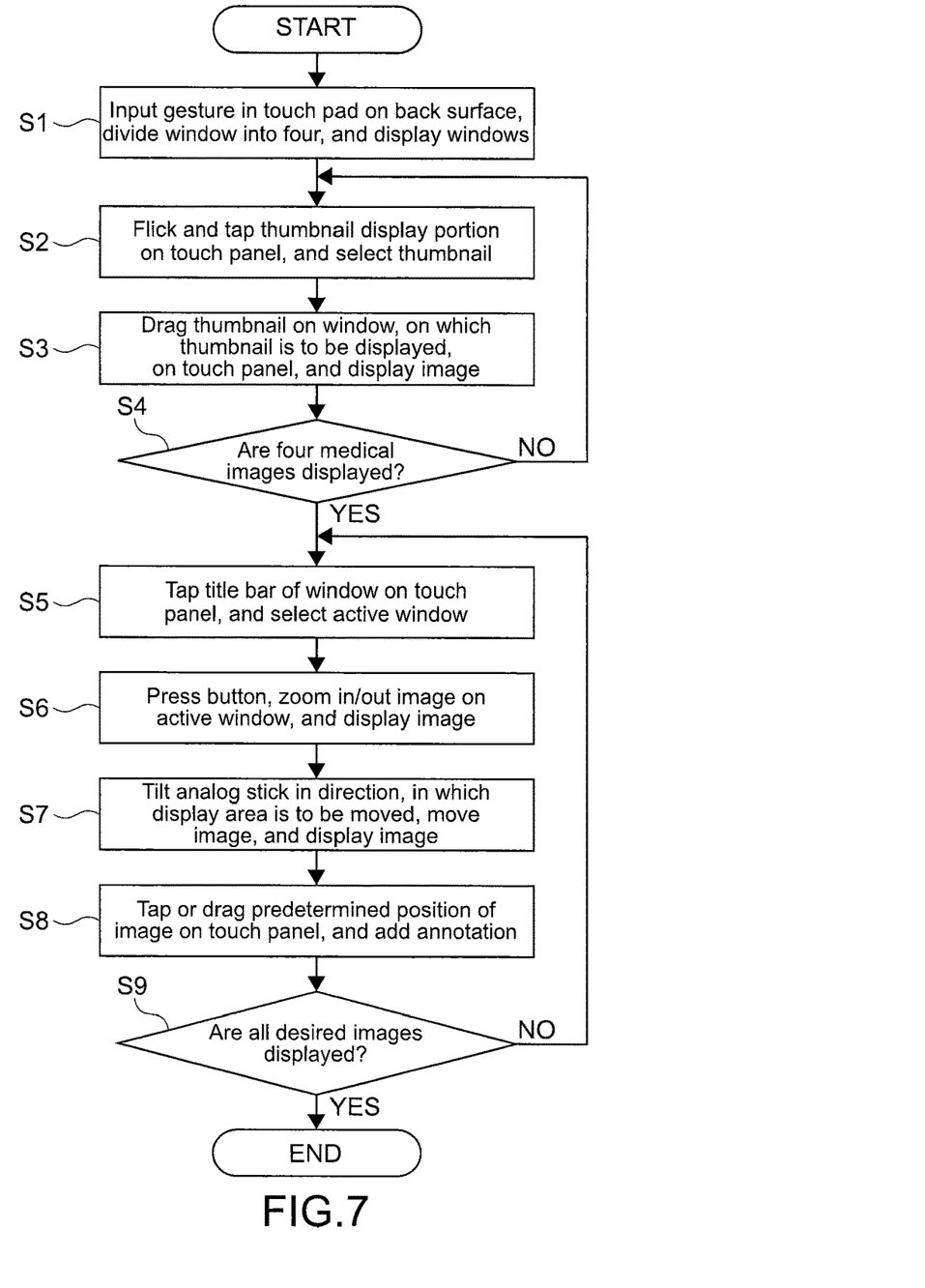
FIG. 7 is a flowchart showing the flow of operation of selecting a medical image by using the input apparatus 100, observing the selected medical image, and adding an annotation to the observed medical image.

Next, an example of the following operation will be described. A medical image is selected by using the input apparatus 100. The selected medical image is observed. An annotation is added to the observed medical image. FIG. 7 is a flowchart showing the flow of operation of selecting a medical image by using the input apparatus 100, observing the selected medical image, and adding an annotation to the observed medical image.

First, a user inputs gesture of "4" in the touch pad TD, which is on the back surface of the input apparatus 100, in order to divide the window LW into four. The window LW is used to observe a medical image. The touch pad TD transmits the input to the controller 11 via the touch screen controller 15.

The controller 11 changes the number of the windows WD, which are displayed on the touch panel TP, to "four" via the display I/F unit 14 (Step S1). Further, the instruction to divide the window LW into four is transmitted to the viewer of the viewer computer 200 via the wireless LAN unit 13. The window LW on the viewer is also divided into four.

Next, a user flicks and taps the thumbnail SN portion on the left portion of the display DP0 of the touch panel TP, in order to select medical images, which are to be displayed on the four windows LW and are to be observed (Step S2). Note that, here, to make description simple, an appropriate tray TR, which includes a set of medical images, is already selected. It is not necessary to select a tray TR here.

Next, a user drags and drops the thumbnail SN, which shows the selected medical image, on the window WD corresponding to the predetermined window LW, on the touch panel TP. This operation is to select the window LW, on which the selected medical image is displayed (Step S3). This operation is transmitted to the controller 11 via the touch screen controller 15. The controller 11 analyzes the input.

The controller 11 analyzes the input, to thereby obtain information that which medical image is displayed on which window WD. So the controller 11 sends the information to the viewer computer 200 via the wireless LAN unit 13. The viewer computer 200 changes an image displayed on the display unit 26 based on the received information. The viewer computer 200 displays the selected medical image on the window LW corresponding to the selected window WD.

The controller 11 obtains the medical image, which is displayed on the window LW, from the viewer computer 200. The controller 11 creates a low-resolution image of the obtained image. The controller 11 displays the low-resolution image on the window WD, which corresponds to the window LW on which the medical image is displayed, via the display I/F unit.

A user repeats the operation of Steps S2 and S3 until medical images to be observed are displayed on all the four windows LW (Step S4).

Next, a user taps a title bar of the window WD on the touch panel TP and selects an active window, in order to select one of the four windows LW and to display an image on the selected window LW (Step S5). Information that which window WD is activated is transmitted to the viewer of the viewer computer 200. The target window LW is activated. Operation on the window LW is allowed.

Next, a user presses the button BT of the input apparatus 100, in order to zoom in/out the medical image, which is displayed on the selected active window LW (Step S6). The zoom in/out instruction input via the buttons BT is transmitted to the viewer of the viewer computer 200. The image displayed on the display unit 26 is changed. In addition, the controller 11 changes the image displayed on the touch panel TP.

Next, a user tilts the analog stick AS, in order to change the display area of the medical image displayed on the selected window LW (Step S7). Similar to Step S6, the image displayed on the active window LW on the display unit 26 is changed. In addition, the image displayed on the active window WD on the touch panel TP is changed.

Next, a user taps or drags a predetermined position on the touch panel TP, in order to add an annotation to the predetermined position of a medical image (Step S8). Because of this operation, information on a position, on which an annotation is added, is transmitted to the viewer of the viewer computer 200. As a result, it is possible to add an annotation to an appropriate position.

A user activates the four windows LW in turn, and executes the operation of Steps S5 to S8 (Step S9).

Described above is an example of operation of selecting a medical image by operating the input apparatus 100, observing the selected medical image, and adding an annotation to the observed medical image.

[Other Configurations of this Technology]

Note that this technology may adopt the following configurations.

(1) An input apparatus, comprising:
  a touch panel configured to receive input operation of at least selecting a medical image, the medical image being displayed on a display area of a display apparatus; and
  an operation input unit configured to receive spatial operation of the medical image as continuous input, the medical image being displayed on the display area.

(2) The input apparatus according to (1), wherein
  the operation input unit is configured to receive an instruction to change a display area of the medical image as the spatial operation of the medical image, the medical image being displayed on the display area, the instruction being at least one of instructions to zoom in/out, move, and rotate the medical image.

(3) The input apparatus according to (1) or (2), further comprising:
  a display unit spatially corresponding to the touch panel; and
  a controller configured
    to display a set on the display unit, the set being a group of at least one medical image,
    to display a low-resolution window on the display unit, the low-resolution window being a low-resolution image of a display area on the display apparatus,
    to send an instruction to the display apparatus to call up a medical image on the display area of the display apparatus, the medical image being selected from the displayed set by a user via the touch panel, and
    to display an image on the low-resolution window, the image being a low-resolution image of the medical image.

(4) The input apparatus according to (3), wherein
  the controller is configured
    to display, on the display unit, a thumbnailed medical image in the set,
    to detect that a user flicks and taps the thumbnail displayed on the touch panel to thereby select the thumbnailed medical image, and
    to display a medical image on the display unit, the medical image corresponding to the thumbnailed medical image.

(5) The input apparatus according to (3) or (4), further comprising:
  a case accommodating the touch panel, the operation input unit, and the display unit, wherein
  the touch panel is arranged on one main surface side of the case, and
  the input apparatus further comprises a touch pad, the touch pad being configured to receive at least selection of the medical image, the touch pad being arranged on a second main surface of the case, the second main surface being opposite to a first main surface, the touch panel being arranged on the first main surface.

(6) The input apparatus according to (5), wherein
  the controller is configured
    to recognize handwritten data, the data input in at least one of the touch panel and the touch pad, and
    to reflect the recognized data in display on the display apparatus.

(7) The input apparatus according to (6), wherein
  the controller is configured
    to recognize the data as a numerical value, and
    to divide the display area into a number, the number corresponding to the recognized numerical value.

(8) An information processing system, comprising:
  a display apparatus including a display area, a medical image being displayed on the display area; and
  an input apparatus including
    a touch panel configured to receive input operation of at least selecting a medical image, the medical image being displayed on the display area, and
    an operation input unit configured to receive spatial operation of the medical image as continuous input, the medical image being displayed on the display area.

[Supplementary Note]

It should be understood by those skilled in the art that various modifications, combinations, sub-combinations and alterations may occur depending on design requirements and other factors insofar as they are within the scope of the appended claims or the equivalents thereof.

The present disclosure contains subject matter related to that disclosed in Japanese Priority Patent Application JP 2012-149725 filed in the Japan Patent Office on Jul. 3, 2012, the entire content of which is hereby incorporated by reference.

What is claimed is:

1. A display control device, comprising:
 a first display;
 a second display separate from the first display;
 an input device including:
  a touch panel integral with the first display and configured to receive a touch operation, and
  an analog stick laterally displaced from the first display along a surface of the display control device and configured to receive an analog operation;
 a first display control circuit configured to display at least one thumbnail image on the first display, respective ones of the at least one thumbnail image corresponding to at least one tissue slide image, and to receive a first input operation of at least selecting one or more of the at least one thumbnail image but not to receive a spatial instruction to change a portion of the one or more tissue slide images as being displayed on the second display, the first input operation including the touch operation on the first display; and
 a second display control circuit separate from the first display control circuit, the second display control circuit being further configured to display one or more of the at least one tissue slide image corresponding to a portion of the selected one or more thumbnail images on the second display, and to receive the analog operation including the spatial instruction but not to receive the first input operation, the spatial instruction including at least one of an instruction to zoom in or out, and an instruction to shift the portion being displayed,
 wherein the touch panel is operable at the same time that the analog stick is operable,
 wherein respective ones of the at least one thumbnail image correspond to tissue slide images different from one another,
 wherein the first input operation and the analog operation are two different kinds of input operations on two different portions of the display control device, and
 wherein the second display control circuit is configured to display an annotation at a predetermined position of the one or more tissue slide images.

2. The display control device according to claim 1, wherein
 the spatial instruction includes an instruction to rotate the portion of the one or more tissue slide images.

3. The display control device according to claim 1, wherein
 the first display control circuit is configured to display a set on the first display, the set being a subgroup of the at least one thumbnail image respectively corresponding to a subgroup of the at least one tissue slide image.

4. The display control device according to claim 1, wherein
 the first input operation includes flick and tap operations on the first display.

5. The display control device according to claim 1, wherein
 the first display control circuit is configured to recognize handwritten data.

6. The display control device according to claim 1, wherein the second display control circuit is configured to receive a second input operation and to add the annotation to the predetermined position of the one or more tissue slide images, the second input operation including a touch operation on the second display.

7. The display control device according to claim 6, wherein the second input operation includes tap or drag operations on the second display.

8. The display control device according to claim 1, wherein the first display and the second display are contiguous.

9. The display control device according to claim 1, wherein the second display has a larger size than the first display.

10. The display control device according to claim 1, wherein the first display is integral with the display control device.

11. The display control device according to claim 1, wherein the second display is external to the display control device, and the display control device is connected to the second display via a wireless communication technology.

12. An information processing system, comprising:
 a processor;
 a first display;
 a second display separate from the first display;
 an input device including:
  a touch panel integral with the first display and configured to receive a touch operation, and
  an analog stick laterally displaced from the first display along a surface of the information processing system and configured to receive an analog operation; and
 a memory coupled to the processor, the memory including a non-transitory computer-readable medium storing instructions that, when executed by the processor, cause a display control circuit of the information processing system to:
  display at least one thumbnail image on the first display, respective ones of the at least one thumbnail image corresponding to at least one tissue slide image, and to receive a first input operation of selecting one or more of the at least one thumbnail image but not to receive a spatial instruction to change a portion of the one or more tissue slide images as being displayed on the second display, the first input operation including the touch operation on the first display, and
  display one or more of the at least one tissue slide image corresponding to a portion of the selected one or more thumbnail images on the second display, and to receive the analog operation including the spatial instruction but not to receive the first input operation, the spatial instruction including at least one of an instruction to zoom in or out, and an instruction to shift the portion being displayed,
 wherein the touch panel is operable at the same time that the analog stick is operable,
 wherein respective ones of the at least one thumbnail image correspond to tissue slide images different from one another,
 wherein the first input operation and the analog operation are two different kinds of input operations on two different portions of the display control device, and
 wherein the second display control circuit is configured to display an annotation at a predetermined position of the one or more tissue slide images.

13. The information processing system according to claim 12, wherein the spatial instruction includes an instruction to rotate the portion of the one or more tissue slide images.

14. The information processing system according to claim 12, wherein the display control circuit is configured to display a set on the first display, the set being a subgroup of the at least one thumbnail image respectively corresponding to a subgroup of the at least one tissue slide image.

15. The information processing system according to claim 12, wherein the first input operation includes flick and tap operations on the first display.

16. The information processing system according to claim 12, wherein the display control circuit is configured to recognize handwritten data.

17. The information processing system according to claim 12, wherein the display control circuit is configured to receive a second input operation and to add the annotation to the predetermined position of the one or more tissue slide images, the second input operation including a touch operation on the second display.

18. The information processing system according to claim 17, wherein the second input operation includes tap or drag operations on the second display.

19. A display control device, comprising:
a processor;
a first display;
a second display separate from the first display;
an input device including:
  a touch panel integral with the first display and configured to receive a touch operation, and
  an analog stick laterally displaced from the first display along a surface of the display control device and configured to receive an analog operation; and
a memory coupled to the processor, the memory including a non-transitory computer-readable medium storing instructions that, when executed by the processor, cause a display control circuit of the display control device to:

display at least one thumbnail image on the first display, respective ones of the at least one thumbnail image corresponding to at least one tissue slide image, and to receive a first input operation of at least selecting one or more of the at least one thumbnail image but not to receive a spatial instruction to change a portion of the one or more tissue slide images as being displayed on the second display, the first input operation including the touch operation on the first display; and display one or more of the at least one tissue slide image corresponding to a portion of the selected one or more thumbnail images on the second display, and to receive the analog operation including the spatial instruction but not to receive the first input operation, the spatial instruction including at least one of an instruction to zoom in or out, and an instruction to shift the portion being displayed, wherein the touch panel is operable at the same time that the analog stick is operable, wherein respective ones of the at least one thumbnail image correspond to tissue slide images different from one another, wherein the first input operation and the analog operation are two different kinds of input operations on two different portions of the display control device, and wherein the second display control circuit is configured to display an annotation at a predetermined position of the one or more tissue slide images.

* * * * *